US006589194B1

(12) United States Patent
Calderon et al.

(10) Patent No.: US 6,589,194 B1
(45) Date of Patent: Jul. 8, 2003

(54) SELF-POWERED COMPRESSION DEVICES AND METHODS FOR PROMOTING CIRCULATION AND THERAPEUTIC COMPRESSION

(75) Inventors: Noam A. Calderon, Haifa (IL); Assaf Ben Arye, Zichron Yakov (IL)

(73) Assignee: C-Boot Ltd, Haifa (IL)

( * ) Notice: Subject to any disclaimer, the term of this patent is extended or adjusted under 35 U.S.C. 154(b) by 0 days.

(21) Appl. No.: 09/602,224

(22) Filed: Jun. 23, 2000

(51) Int. Cl.[7] .............................. A61H 9/00; A61F 5/00
(52) U.S. Cl. .......................................... 601/151; 602/13
(58) Field of Search ................................ 601/148–153, 601/27; 602/13; 128/DIG. 20

(56) References Cited

U.S. PATENT DOCUMENTS

| | | | | | |
|---|---|---|---|---|---|
| 1,608,239 | A | * | 11/1926 | Rosett | |
| 2,543,284 | A | * | 2/1951 | Gleason | 601/152 |
| 3,654,919 | A | * | 4/1972 | Birtwell | 601/152 |
| 3,826,249 | A | * | 7/1974 | Lee et al. | 601/148 |
| 3,865,102 | A | * | 2/1975 | Birtwell | 601/152 |
| 4,029,087 | A | * | 6/1977 | Dye et al. | 128/24 R |
| 4,372,297 | A | * | 2/1983 | Perlin | 128/64 |
| 4,624,244 | A | * | 11/1986 | Taheri | 128/24 R |
| 4,781,189 | A | * | 11/1988 | Vijil-Rosales | 128/327 |
| 4,841,956 | A | * | 6/1989 | Gardner et al. | 128/64 |
| 4,947,834 | A | * | 8/1990 | Kartheus et al. | 128/64 |
| 5,403,265 | A | * | 4/1995 | Berguer et al. | 601/151 |
| 5,711,760 | A | * | 1/1998 | Ibrahim et al. | 601/149 |
| 5,938,627 | A | * | 8/1999 | Hickman | 601/149 |
| 6,409,691 | B1 | * | 6/2002 | Dakin et al. | 602/13 X |

FOREIGN PATENT DOCUMENTS

| | | | | |
|---|---|---|---|---|
| EP | 0039629 | * | 11/1981 | |
| GB | 817521 | * | 7/1959 | 601/149 |
| GB | 2253405 A | * | 7/1993 | 601/149 |
| NL | 0 168 085 | * | 1/1986 | A61H/23/04 |

* cited by examiner

*Primary Examiner*—Denise M. Pothier
(74) *Attorney, Agent, or Firm*—Rashida A. Karmali

(57) ABSTRACT

A self-powered compression device for use in promoting circulation, said device embodying a plurality of inflatable sleeves arranged sequentially for applying compression to a body or limb and which further comprises a pump, a piping system and a bandage or boot to enclose the device in its entirety. A method for using self-generated pressure in promoting circulation in conditions including but not limited to, lymphatic and traumatic edemas, venous disorders, limb ulcers, varicose veins, muscle fatigue, sports medicine, cellulite treatment, diabetic feet, feet massage for recreation or cosmetic enhancements.

14 Claims, 2 Drawing Sheets

SELF-POWERED COMPRESSION DEVICES AND METHODS FOR PROMOTING CIRCULATION AND THERAPEUTIC COMPRESSION

1. FIELD OF THE INVENTION

The present invention relates to self-powered compression devices and methods for promoting circulation and therapeutic compression in mammals in general or an individual in need thereof. More particularly, the invention is in the class of medical devices, comprising a shoe, a plurality of sleeves or limb massager, which utilizes sequential, cyclical pressure, energy or vector forces, to aid circulation in a body part such as the limbs of a mammal. The inflatable sleeves or pockets are filled with air by a pumping means. The inflatable sleeves transmit massaging movement to the vessel walls whenever the individual wearing the device moves. The pressure generated is a function of the user's body weight and gravitational force. The present invention further provides methods to harness energy generated during movement and weight transfer and uses the energy for compressing to create a massaging effect on the circulation and the muscular-skeletal system.

2. BACKGROUND OF THE INVENTION

There are many patented devices that apply cyclic pressure to a mammal's limbs-legs, arms and/or feet. Many have used pulsating pads or plunges for improving circulation. Elastic and non-elastic stockings are widely employed in support and compression therapy of the foot and ankle. Others have used hydraulic and pneumatic bladders for the same and for many other purposes. The shapes, sizes and composition of such bladders and pads are widely varied, depending largely on their particular application. Most suffer varying degrees of shortcomings, including ineffectiveness, difficulties in application and removal, lack of controlled adjustability, loss of compression, excessive sweating, foul odor and discomfort.

U.S. Pat. Nos. 5,120,300 and 5,254,122 relate to therapeutic devices capable of applying therapeutic compression to the body, particularly the limbs, arms and/or feet, in which the user applies non-elastic therapeutic compression band by band, and the user can tighten the compression bands to control the non-elastic pressure. The cyclical or sequential compression of limbs improves blood fluid returns for reducing edema and improving healing. U.S. Pat. No. 5,897,518 describes a foot and ankle-therapeutic compression device in which a pair of foot and ankle compression bands are tightened and anchored in tightened condition by VELCRO hook and loop surfaces.

The present invention is directed towards improving the cyclical or sequential compression. The pressure is uniquely generated by body muscle action and flexing of the limbs to provide improved circulation and healing in a variety of peripheral vascular diseases in mammals.

3. SUMMARY OF THE INVENTION

The self-powered compression device of the present invention permits the wearer of a plurality of inflatable pockets that form a sleeve around the limb to apply a controlled level of circular compression to the limb.

The self-powered system comprises inflatable or pneumatic sleeves which wrap around the limb adopting the wearer's shape of:the limb. Energy is generated by the wearer's muscle action, weight bearing gravity force and constant transfer of body weight during walking, moving or flexing of the limbs. The energy generated is transmitted to the air or liquid inflated sleeves or pockets which are installed to surround the limb. As a result of the cyclical and sequential movement of the pockets from the lower portion of the limb towards its upper portion, vector forces are generated. The resulting compression preserves the venous reflex and aids venous flow back from the foot in the direction of the heart. The cyclical pumping action causes the pocket furthest from the heart to inflate first and reach a preset pressure. This is followed by the inflation of the successive sleeve. This in turn reaches a preset pressure, thereby triggering the next sleeve in succession to inflate and continue the cyclical compression action. Thus, the pumping or compression device that inflates the pockets is driven by the wearer's muscle movement and is a function of the wearer's weight and flexure of the wearer's limbs.

The successive inflating of the pockets or sleeves regulates the pressure and generates a differential pressure ("delta"). The delta pressure, in turn, creates a massaging effect that aids the lymphatic drainage, venous return, capillary flow, and improves even the heart preload pressure. The convenience of this device is that the inflatable sleeves are mounted in the shape of the wearer's shoe or boot, and thus provide a system that the wearer can use at any time or place during the course of daily activities. The comfort that this compression device affords and the ease with which the wearer can maintain a controlled compression level at all times is an important advantage over conventional foot and leg compression devices.

In a preferred embodiment, the present invention further comprises of a device and methods in which an external or passive working pressure is applied. "Passive" working pressure as used herein, indicates that the user does not have to move to generate the pressure, but that it is applied by an electrical or mechanical tuning set up.

In another embodiment, the present invention comprises of a plurality of inflatable sleeves including a set of distal sleeves located furthest from the heart and a set of proximal sleeves located closest to the heart, whereby the proximal sleeve functions as a no-return valve when the remaining sleeves deflate, before the next cycle starts.

In yet another embodiment, the present invention comprises of a device and methods representing an assembly of sleeves especially designed to apply massage to a cellulite rich region of the body, for example, in the trochanteric region, as part of a cellulite treatment protocol.

In an additional embodiment, the device and methods of the present invention comprise of a dynamic foot support including a plurality of sleeves and pump, both relatively small in size and suitable for diabetic patients.

In an additional embodiment, the device and methods of the present invention are assembled for use in recreational massaging or for general good health practice. The inflatable sleeves may be lined with a series of small magnets to stimulate blood circulation A primary object of the invention is to provide a small, lightweight and comfortable device suitable for prolonged wear, and methods which helps prevent and/or solve many of the problems associated with impaired circulation.

Another object includes providing a compression device which encloses only limited portions of the limb, especially those portions in need of improving circulation. Related objects include providing comfort and moisture control and avoiding the need for accessories such as additional wraps, straps, stockings or sandals.

Another object of the present invention is to provide a cyclical compression device requiring a minimum volume of air per pulsation.

Another object is to provide an aid for blood and lymphatic circulation which fits a wide range of patients without requiring custom-made modifications in the system.

Another object of the invention is to provide a light, portable and circulation improvement device, which is affordable, easy to clean, reusable or disposable.

The present invention provides compression methods and devices using muscle and motion generated energy or power to promote circulation in general, and has applications in a variety of conditions including, but not limited to, lymphatic and traumatic edemas, venous disorders, limb ulcers, diabetic feet, varicose veins, muscle fatigue, sports medicine, cellulite treatment or cosmetic enhancements.

The present invention describes methods and: a compression device comprising a set of inflatable pockets having an outlet valve, and inlet valve, an exhaust valve, a bandage and a pump mounting means, providing a stabile, portable, economical and efficient device.

Numerous other features, advantages, and objects of the invention will be evident from the following more detailed description of certain preferred embodiments. Particularly when considered together with the accompanying drawings and appended claims.

4. BRIEF DESCRIPTION OF THE DRAWINGS

5. DETAILED DESCRIPTION OF THE PREFERRED EMBODIMENTS

Figure 1:
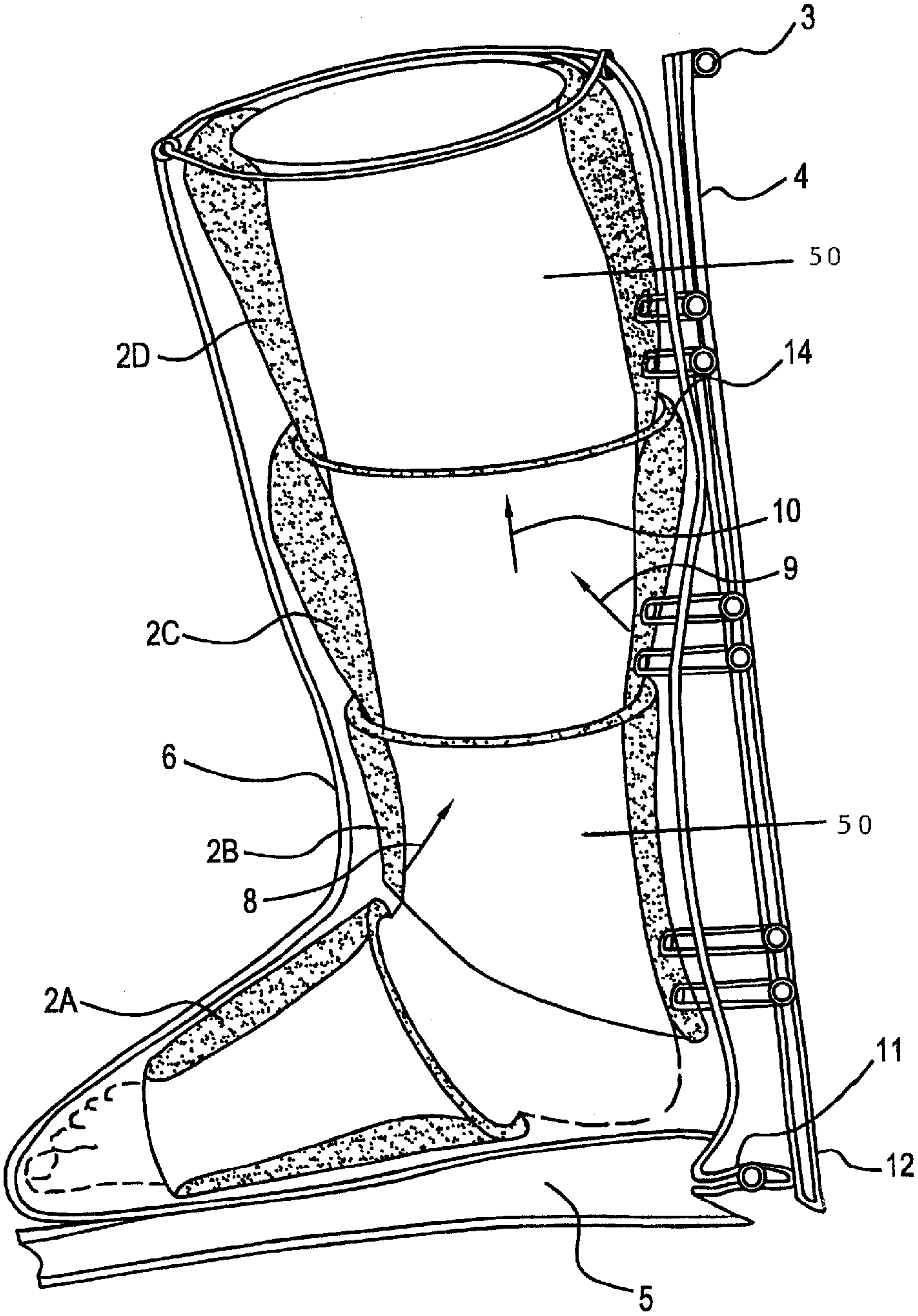
FIG. 1 shows a lateral view of an embodiment of the present invention comprising of a pump, bandage, inflatable pressure sleeves, a pneumatic pipe system, an outlet valve, an inlet valve and an exhaust valve.

The compression device embodying the present invention, shown in the drawings as a shoe, boot, and/or stockings is an assembly made up of a plurality of pressure sleeves 2A, 2B, 2C, 2D and 2E arranged in sequence. The sleeves consist of a plurality of rigid coins (50), said coins adapted to configure to the shape of the body such that upon walking vector forces are generated by weight changes, said forces being transmitted through the coins, thereby causing a circular pressure and promoting circulation. A linkage between the sleeves, that are located in close contact, causes transmission of vector forces and energy from one sleeve of coin to another.

Figure 2:
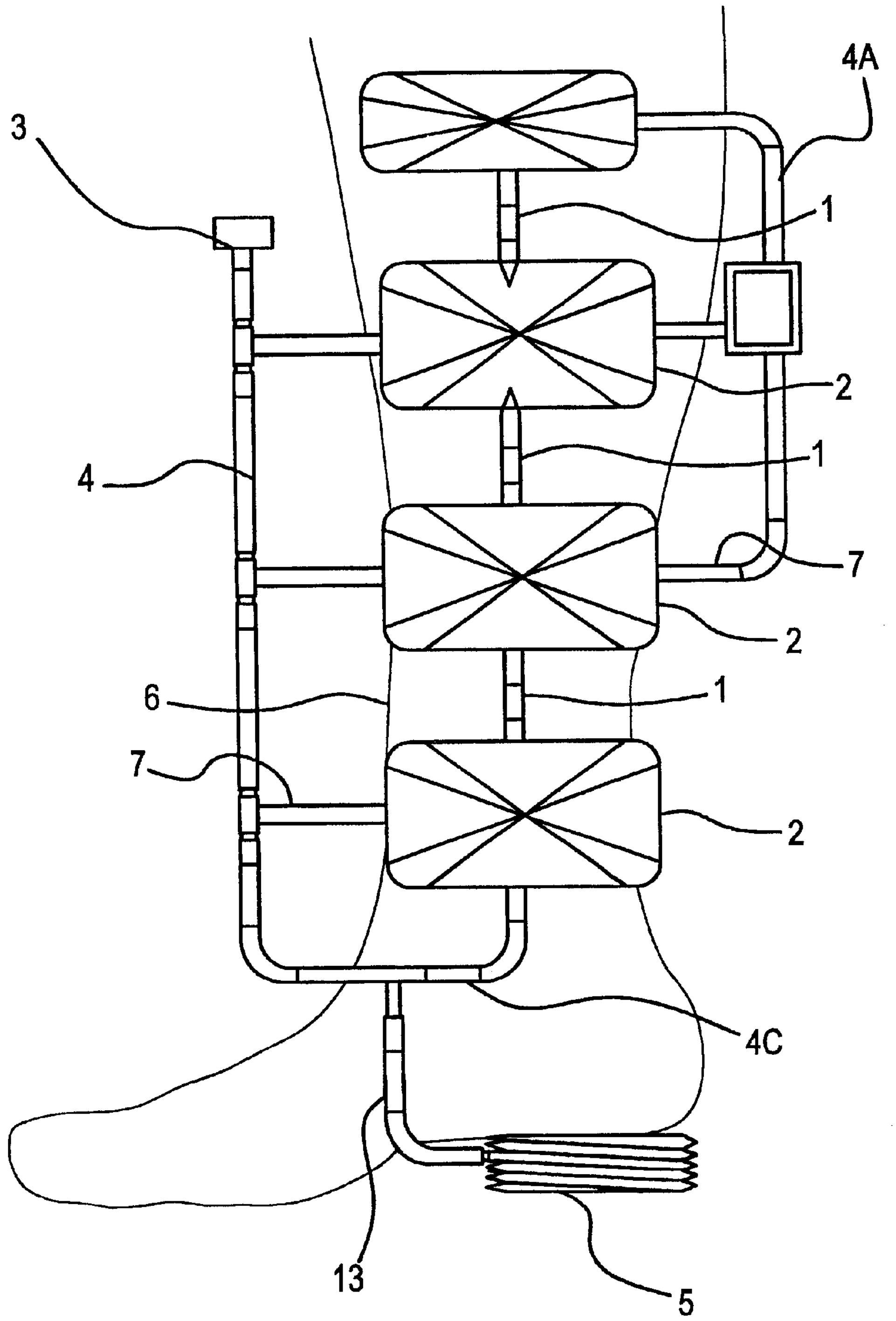
FIG. 2 shows a lateral view of a different embodiment showing the structure of the pipe system for the device.

Referring to FIG. 1, these pressure sleeves are in edge-to-edge relationship to encompass and surround the whole limb. Referring to FIG. 1 and FIG. 2 each pressure sleeve has an inlet valve 1 which is used to inflate the sleeve with air or liquid, and an outlet valve 7 which allows the air or liquid to flow out in a sequential and cyclical pumping action. When the wearer flexes the muscles, as in walking or shift in weight, the resulting vector forces 8 and 9, create a compression and massaging effect in the direction 10, flowing from the distal sleeve 2A to the proximal sleeve 2D, which is closest to the heart. The sleeves are preferably made of a strong elastic or non-elastic material. The inner surface is preferably relatively smooth to engage the skin or a sock or stocking. The outer surface of the sleeves has a fastening surface thereon, preferably facilitating the wrapping of a bandage 6 around the whole shoe and/or boot. As shown in FIG. 1, it is applied continuously along the outer surface, that is, the surface opposite the surface which interfaces with the body.

6. EXAMPLES

The compression devices and methods of the present invention may be used to promote circulation in general, in a number of conditions including, but not limited to, the prevention and treatment of lymphatic and traumatic edemas, venous disorders, limb ulcers, varicose vein prevention and treatment, circulation stimulation and muscle toning, sports medicine applications or cosmetic cellulite treatment or enhancements.

Lymphedema, chronic swelling of extremity, can have serious complications, including skin lesions, fibrosis and an increased risk of infections due to accumulation of protein-rich fluid in the interstitial spaces. In children, primary lymphedema resulting form abnormal development of the lymphatic system is the most common form.

Secondary, lymphedema results when an inflammatory or mechanical obstruction of the lympatics occurs from trauma, regional lymph node resection or irradiation or involvement of nodes by malignancy.

Secondary, dilation of the lymphatics that occurs in both forms leads to incompetence of the valve system, disrupting the orderly flow along the lymph vessels, and results in progressive stasis of a protein-rich fluid, with secondary fibrosis. Hypertrophy of the limb results, with markedly thickened and fibrotic skin and subcutaneous tissue and diminution in the fatty tissue. The treatment of lymphedema is often not very satisfactory. Some of the patients can be treated with one of the following measures: 1) the flow of lymph out of the extremity can be aided through intermittent extortion of the extremity, especially during the sleeping hours; use of elastic bandages or fitted heavy-duty elastic stocking; and massage toward the trunk, either by hand or by means of pneumatic pressure devices designed to milk edema out of an extremity. 2) Secondary cellulitis should be treated by adequate rest, elevation and antibiotics. 3) Course of diuretic therapy in those with premenstrual or seasonal exacerbations. 4) Operative procedures for peripheral lymedema in whom non-operative treatment has failed. Amputation is used as a last resort in very severe forms.

However, bed rest with elevation of the limb greatly restricts activities of daily living. There are various external pneumatic compression devices on the market, but these procedures almost exclusively require the individuals to be hospitalized and/or to be under the care of a physiotherapist. In other words, such treatment protocols greatly restrict activities of daily living.

The compression devices of the present invention are designed to fit comfortably on the wearers limb and are self-powered by the energy generated by muscle action and flexure of the limb.

Vascular malformations are disorders involving arteries, veins and sometimes capillaries and lymphatics. The importance of exogenous influences during the early embryonic life, especially of viral infectious, toxic substances, drugs and trauma, has been emphasized. In venous malformations, another common feature is the formation of the thrombi and their calcification into phleboliths. In arterovenous shunts the venous segment may show a reactive hyperplasia of the smooth muscle and elastic tissue. In later stages, the venous wall undergoes degenerative changes such as medial and intimal fibrosis. Phlebosclerosis is a common alteration on non-varicose and varicose veins. It is found with equal prevalence in all the segments of the long saphenous vein and in smaller superficial vein branches. Intimal fibrosis predominates over medical and adventitial fibrosis and is more conspicuous in the superficial than in the deep leg veins. It occurs in the majority of the aging population.

The causes for lymphedemas are inflammatory diseases of lymphatics and lymph nodes form infections, tumor compression of lymph nodes, trauma and destruction of lymph nodes and lymphatics. A combination of dilated lymph capillaries with partly dilated interendothelial spaces with an intra-and pericapilary edema is indicative of lymphedema. Peripheral lymph collectors are distinguished from veins by their structure and contents. The ventromedical prefascial bundle runs form the dorsum pedis to the medial side of the lower leg and along the great saphenous vein to the groin. It contains two to seven collectors each with a diameter of 0.2–0.5 mm. The lymphatics lie either directly above the fascia or halfway between the fascia and dermis. The dorsolateral prefascial bundle consists distally of three to four collectors merging to become a single channel that runs alongside the short saphenous vein to the popliteal groove. The deep collectors accompany the three leg arteries and the femoropopliteal artery before finally reaching the lingual lymph nodes. They lie between the artery and vein or lateral to the artery. In contrast to venous drainage, the lymphatic flow runs from the deep into the superficial lymphatic system and form these into the inguinal lymph nodes. Therefore, it is essential that the compression device of the present invention is designed accordingly by wrapping the inflatable sleeves in the complete structure of the boot to facilitate the approximate self-powered compression in the diseased limb.

Although trauma, tumor and infection are significant disease entities that can require amputation, over 90% of all limb amputations in the Western world occur as a direct or indirect consequence of peripheral vascular disease and/or diabetics. The mainstay of medical management is to postpone amputation by relieving pain or improving the local blood flow in the limb. A broad range of anticoagulant agents have been tested and synthetic analogues or prostacyclins offer most hope. The compression device of the present invention, used in combination with an effective anticoagulant stimulates the healing and treatment of peripheral vascular disease in mammals.

The breakdown of the foot in the diabetic patient is commonly due to a combination of neuropathy, infection and/or some vascular impairment. If an ingrown toenail or ulcer occurs and remains untreated because of a lack of pain sensation, the infection may spread throughout the foot, creating a cross infection that demands more blood supply than the impaired, vessels can provide. The resulting gangrene may demand an amputation. The device and methods of the present invention are designed to improve the vascular and lymphatic circulation and to provide a massaging and toning effect on the muscular-skeletal system. Thus, they are ideally suited to prevent and treat vascular arterial pathologies in the diabetic individual, and to prevent a constant pressure of the foot by means of a dynamic inflatable foot support.

The present compression devices and methods are convenient to operate and use in normal routine life style and are adaptable for each user's needs. They require no fixed and stationary stations to provide energy, are cheap to produce and can shorten the time needed for hospitalization. Moreover, they do not suffer from the disadvantages of the models described in the prior art, for example, of tight elastic bandages which cause sweating and foul odor. In fact, the present device and methods are even suitable for improving circulation in women who are pregnant, individuals with varicose veins or spider veins, individuals doing heavy exercise, and even in surgical patients having undergone a vein harvest for cardiac surgery after angina pectoris or congestive heart failure.

TREATMENT AND PREVENTION OF VENOUS INCOMPETENCE

The compression device and methods of the present invention are illustrated by way of protocols for some patients suffering from venous incompetence. The prototypes of the embodiments described in FIG. 1 and FIG. 2 were built and used in the patients suffering from poor circulation. The clinical symptoms and biochemical parameters are recorded before and at regular intervals after the patients have been using them when getting around in their daily activities. It is believed that the device of the present invention may completely inhibit and/or prevent venous incompetence in vivo in patients. When another therapeutic regimen such as a chemotherapeutic agent is administered along with the use of present invention, it is used in dosages known to those skilled in the art. The present invention is not to be limited in scope by the embodiment disclosed in the example which is intended as an illustration of one aspect of the invention and any methods and devices which are functionally equivalent are within the scope of the invention. Indeed, various modifications of the invention in addition to those shown and described herein will become apparent to those skilled in the art from the foregoing description. Such modifications are intended to fall within the scope of the appended claims.

What is claimed is:

1. A self-powered compression device comprising a plurality of sleeves, each of said sleeves being individually separated and filled with air, and constructed individually to configure to the shape of a body upon which the sleeves are wrapped, each sleeve being positioned in contact with the adjacent sleeves to form a linkage, said linkage enabling a transmission of vector forces and energy from one sleeve to another sleeve, a safety system to control the pressure in each sleeve, a pressure pump sized and configured to be located beneath the foot arch or the heel, said pump being linked to each sleeve by a piping system, said piping system being connected separately by separate valves to each of said sleeves, wherein the pressure differential is sufficient to exert a massaging force on the limb in a sequential and cyclical order, thereby promoting circulation of venous, lymphatic, arterial or interstitial fluid and a boot sole sized and configured to be located under the foot, the boot sole including the pressure pump and the boot sole not united with the inside of the boot device to ensure the pump does not interfere with the operation of the sleeves.

2. The self-powered compression device according to claim 1, further comprising a bandage of non-elastic material, said bandage being wrapped around the sleeves and designed to produce a milking effect of the body part by means of the cyclical compression pressure.

3. The self-powered compression device according to claim 1, wherein the cyclical pressure on the sleeves is operatively associated with the movement of the body and to the transfer in body weight during stepping and walking.

4. The self-powered compression device according to claim 1, wherein the sleeves are inflated with air or liquid.

5. The self-powered compression device according to claim 1, wherein the plurality of sleeves and the pumping means are enclosed in a boot, said boot constructed of a non-elastic material.

6. The self-powered compression device according to claim 1, wherein each sleeve is independently inflated to a preset pressure, said pressure being provided by the pump system.

7. The self-powered compression device according to claim 1, wherein the self-powered compression device is used to promote circulation in a variety of conditions including lymphatic and traumatic edemas, venous disorders, limb ulcers, varicose veins, diabetic feet, muscle fatigue, sports medicine, cellulite treatment or cosmetic enhancements.

8. The self powered compression device according to claim 1, comprising a plurality of rigid coins.

9. The self-powered compression device according to claim 8, wherein said sleeves comprise a plurality of variously shaped sleeve members arranged along the length of the leg.

10. The compression device according to claim 9, wherein the plurality of sleeve members are arranged to enable application of cyclic operations resulting in transmission of vector forces and energy from one sleeve member to another, said device further comprising a safety system, said safety system controlling the pressure in each sleeve member individually.

11. The compression device according to claim 8, wherein the plurality of sleeve members are arranged to enable application of cyclic operations resulting in transmission of vector forces and energy from one sleeve member to another, said device further comprising a safety system, said safety system controlling the pressure in each sleeve member individually.

12. The self-powered compression device according to claim 11, wherein the operation of the individual sleeve members results in a cyclical release of air thereby creating a ventilating effect.

13. The compression device according to claim 11, wherein the compression device is used to promote circulation in a variety of conditions including lymphatic and traumatic edemas, venous disorders, limb ulcers, varicose veins, diabetic feet, muscle fatigue, sports medicine, cellulite treatment or cosmetic enhancements.

14. The self-powered compression device according to claim 1, wherein the operation of the individual sleeve members results in a cyclical release of air thereby creating a ventilating effect.

* * * * *